United States Patent [19]
Gordon et al.

[11] Patent Number: 5,902,814
[45] Date of Patent: May 11, 1999

[54] SPIRO-AZABICYCLIC COMPOUNDS USEFUL IN THERAPY

[75] Inventors: John Charles Gordon, Caledonia; Ronald Conrad Griffith, Pittsford; Robert John Murray; Michael Balestra, both of Rochester, all of N.Y.

[73] Assignee: Astra AB, Sodertalje, Sweden

[21] Appl. No.: 08/525,575

[22] PCT Filed: Aug. 22, 1995

[86] PCT No.: PCT/SE95/00937

§ 371 Date: Sep. 18, 1995

§ 102(e) Date: Sep. 18, 1995

[87] PCT Pub. No.: WO96/06098

PCT Pub. Date: Feb. 29, 1996

[30] Foreign Application Priority Data

Aug. 24, 1994 [GB] United Kingdom .................... 9417084
Mar. 8, 1995 [GB] United Kingdom .................... 9504627

[51] Int. Cl.⁶ ...................... C07D 498/20; C07D 453/02; A61K 31/445; A61K 31/42
[52] U.S. Cl. ............................ 514/278; 546/18; 546/137; 548/216; 548/512; 514/375
[58] Field of Search ................ 546/18; 514/278; 548/216, 512

[56] References Cited

U.S. PATENT DOCUMENTS 5,073,560  12/1991  Wu ............................................ 546/19
5,137,895   8/1992  Munson .................................. 546/137
5,534,520   7/1996  Fisher ...................................... 546/19

FOREIGN PATENT DOCUMENTS 0337547  10/1989  European Pat. Off. .
0350118   1/1990  European Pat. Off. .
0452101  10/1991  European Pat. Off. .
2505143   8/1975  Germany .
9201690   2/1992  WIPO .
9503303   2/1995  WIPO .

OTHER PUBLICATIONS

Abstract of Taiwan Patent Application No. 201312–A.
Nakanishi, Chem Abs 80, 133284 (1974).
Maillard. Chem Abs 78 71968t (1973).
Trigo, I Het Chem 18, 1507 (1981).
Sivilotti, Science 269, 1681, Sep. 1995.

*Primary Examiner*—Mark L. Berch
*Attorney, Agent, or Firm*—Nixon & Vanderhye

[57] ABSTRACT

There are provided new compounds of formula I:

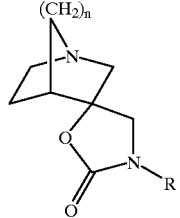

wherein
R represents hydrogen or methyl; and
n represents 1 or 2;
or a pharmaceutically acceptable acid addition salt thereof, together with processes for preparing them, compositions containing them and their use in therapy. Compounds of formula I are expected to be useful in the treatment of psychotic disorders, intellectual impairment disorders and anxiety.

14 Claims, No Drawings

SPIRO-AZABICYCLIC COMPOUNDS USEFUL IN THERAPY

This application is a 371 of PCT/SE95/00937 filed Aug. 22, 1995.

This invention relates to novel compounds, processes for preparing them, compositions containing them and their use in therapy.

Spiro-azabicyclic compounds are known to have therapeutic activity in a range of disorders of the central nervous system. Taiwan Patent Application 201312, European Patent Application 452101 (both of Israel Institute of Biological Research), International Patent Application WO 95/03303 (Israel Institute of Biological Research; published after the earliest priority date of this application) and European Patent Application 350118 (Merck Sharpe and Dohme) disclose azabicyclic compounds including azabicyclo(2.2.2) octane and/or azabicyclo(2.2.1)heptane derivatives spiro-connected to 5-membered rings which have muscarinic agonist activity and which are indicated for the treatment of diseases caused by deficiency in central cholinergic function. European Patent Application 337547 (Merck, Sharpe and Dohme) discloses azabicyclic compounds spiro-connected to 5-membered rings which are antagonists of $5-HT_3$ receptors and which are indicated for the treatment of inter alia schizophrenia, nausea, migraine and Alzheimer's disease.

We have now identified a new group of spiro-azabicyclic compounds which have useful pharmacological properties.

Thus, according to the invention, we provide a compound of formula I:

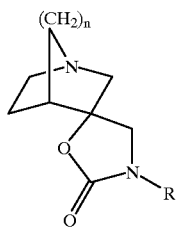

I wherein

R represents hydrogen or methyl; and n represents 1 or 2;

and pharmaceutically acceptable acid addition salts thereof.

We prefer compounds of formula I in which R represents hydrogen. We prefer compounds of formula I in which n represents 2.

As a second aspect of the invention we provide a process for the preparation of a compound of formula I, or a pharmaceutically acceptable acid addition salt thereof, which comprises:

(a) preparing a compound of formula I in which R represents hydrogen by cyclising a corresponding compound of formula II

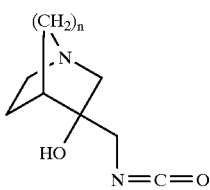

II wherein n is as defined above;

(b) preparing a compound of formula I by reacting a corresponding compound of formula III

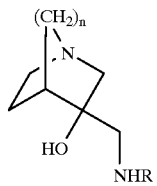

III wherein n and R are as defined above with a carbonyl donating compound; or (c) preparing a compound of formula I in which R represents methyl by alkylating a corresponding compound of formula I in which R represents hydrogen;

(d) preparing one enantiomer of a compound of formula I by resolving the one enantiomer from a mixture of enantiomers;

and where desired or necessary converting the resultant compound of formula I, or an acid addition salt thereof, to a pharmaceutically acceptable acid addition salt thereof, or vice versa.

In process (a) the reaction will take place on warming the compound of formula II in a polar protic solvent e.g. water.

In process (b), examples of carbonyl donating compounds include carbonyldiimidazole, carbonyldichloride (phosgene) and triphosgene. The ring closure reaction will take place on heating or refluxing the compound of formula III with carbonyldiimidazole in a polar organic solvent such as THF for 1–4 hours or until reaction is complete. Alternatively phosgene can be bubbled through a solution of the compound of formula III in an organic solvent such as THF or toluene at elevated temperature for 1–4 hours or until reaction is complete.

In process (c), the alkylation reaction will take place under conditions well known in the art, for example, by treating the compound of formula I in which R represents hydrogen with a strong base followed by a methyl halide e.g. methyliodide.

Compounds of formula II may be prepared by Curtius rearrangement of a compound of formula IV:

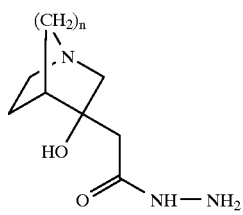

IV wherein n is as defined above.

Typical reaction conditions for the Curtius rearrangement are discussed in J March "Advanced Organic Chemistry" (1985) 3rd Edition, pages 984–5 however we prefer to perform the reaction by treating the compound of formula IV in water with sodium nitrite and warming to approximately 85° C. for approximately 1 hour. The compound of formula II is not isolated and the cyclisation reaction described in process (a) proceeds directly in situ.

Compounds of formula IV may be prepared by treatment of a compound of formula V

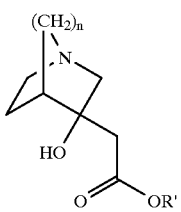

wherein n is as defined above, and R' is an alkyl or aryl group, with anhydrous hydrazine.

This reaction may be performed in a polar protic solvent at ambient temperature over 4–12 hours. We prefer that R' represents alkyl, typically methyl, ethyl or t-butyl.

Compounds of formula V may be prepared by reaction of a compound of formula VI

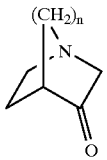

wherein n is as defined above with an acetic acid ester in the presence of n-butyl lithium. The acetic acid ester (for example the t-butyl or ethyl ester) is first treated with n-butyl lithium at −78° C. and the reaction proceeds on adding the compound of formula VI and warming to room temperature. The product is obtained on quenching with water.

Compounds of formula VI are either known or may be prepared by known methods.

Compounds of formula III may be prepared by reacting a compound of formula VII

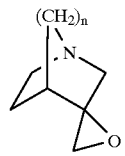

wherein n is as defined above, with ammonia or methylamine.

This reaction may be performed under standard conditions for example by combining the reagents in a polar protic solvent at ambient or elevated temperature.

Compounds of formula III may also be prepared by reacting a compound of formula VI with trimethylsilyocyanide ($Me_3SiCN$) followed by reduction with, for example, lithium aluminium hydride or Raney Nickel. Reaction conditions will be familar to a person skilled in the art.

Compounds of formula VII may be prepared from the corresponding compounds of formula VI using one of the reagents well known in the art for preparation of oxiranes from ketones (see, for example, the reactions referenced in J March "Advanced Organic Chemistry" (1985) 3rd Edition, page 1161). We have found that trimethylsulphoxonium iodide is a suitable reagent and the reaction may be performed in DMSO at a temperature of between room temperature and 80° C. over a period of up to 2 hours, or until reaction is complete.

Acid addition salts of the compounds of formula I which may be mentioned include salts of mineral acids, for example the hydrochloride and hydrobromide salts; and salts formed with organic acids such as formate, acetate, malate, benzoate and fumarate salts.

Acid addition salts of compounds of formula I may be formed by reacting the free base or a salt, enantiomer or protected derivative thereof; with one or more equivalents of the appropriate acid. The reaction may be carried out in a solvent or medium in which the salt is insoluble or in a solvent in which the salt is soluble, eg water, dioxan, ethanol, tetrahydrofuran or diethyl ether, or a mixture of solvents, which may be removed in vacuo or by freeze drying. The reaction may be a metathetical process or it may be carried out on an ion exchange resin.

The compounds of the invention and intermediates may be isolated from their reaction mixtures by standard techniques.

The compounds of formula I exist in tautomeric or enantiomeric forms, all of which are included within the scope of the invention. The various optical isomers may be isolated by separation of a racemic mixture of the compounds using conventional techniques, e.g. fractional crystallisation, or chiral HPLC. Alternatively the individual enantiomers may be made by reaction of the appropriate optically active starting materials under reaction conditions which will not cause racemisation.

Intermediate compounds also exist in enantiomeric forms and may be used as purified enantiomers, racemates or mixtures.

The compounds of the invention are indicated as pharmaceuticals, in particular in the treatment or prophylaxis of psychotic disorders and intellectual impairment disorders. Examples of psychotic disorders include schizophrenia, mania and manic depression. Examples of intellectual impairment disorders include Alzheimer's disease, learning deficit, cognition deficit and attention deficit hyperactivity disorder. The compounds of the invention may also be useful as analgesics and in the treatment or prophylaxis of Parkinson's and Huntington's disease, neurodegenerative disorders in which there is loss of cholinergic synapses, Tourette's syndrome, depression and anxiety. The compounds may further be indicated for the treatment or prophylaxis of jetlag and for use in inducing the cessation of smoking.

According to a further aspect of the invention we provide a compound of the invention for use as a pharmaceutical, especially in the treatment or prophylaxis of the aforementioned diseases or conditions.

For the above-mentioned uses the dosage administered will, of course, vary with the compound employed, the mode of administration and the treatment desired. However, in general, satisfactory results are obtained when the compounds of the invention are administered at a daily dosage of from about 0.1 mg to about 20 mg per kg of animal body weight, preferably given in divided doses 1 to 4 times a day or in sustained release form. For man, the total daily dose is in the range of from 5 mg to 1,400 mg, more preferably from 10 mg to 100 mg, and unit dosage forms suitable for oral administration comprise from 2 mg to 1,400 mg of the compound admixed with a solid or liquid pharmaceutical carrier or diluent.

The compounds of formula I, and pharmaceutically acceptable salts thereof, may be used on their own or in the form of appropriate medicinal preparations for enteral or parenteral administration. According to a further aspect of the invention, there is provided a pharmaceutical formulation including preferably less than 80% and more preferably less than 50% by weight of a compound of the invention in admixture with a pharmaceutically acceptable diluent or carrier.

Examples of diluents and carriers are:
for tablets and dragees: lactose, starch, talc, stearic acid;
is for capsules: tartaric acid or lactose;
for injectable solutions: water, alcohols, glycerin, vegetable oils;
for suppositories: natural or hardened oils or waxes.

There is also provided a process for the preparation of such a pharmaceutical composition which comprises mixing the ingredients.

According to a further aspect of the invention, there is provided the use of a compound of formula I, or a pharmaceutically acceptable salt thereof, in the manufacture of a medicament for the treatment or prophylaxis of one of the above mentioned diseases or conditions; and a method of treatment or prophylaxis of one of the above mentioned diseases or conditions, which comprises administering a therapeutically effective amount of a compound of formula I, or a pharmaceutically acceptable salt thereof, to a patient.

Compounds of formula IV and compounds of formula III in which R represents methyl are new and useful intermediates. Thus a further aspect of the invention we provide a compound of formula IV, or a salt thereof. We also provide compounds of formula III in which R represents methyl, or a salt thereof.

Compounds of formula I are agonists of nicotinic acetylcholine receptors. While not being limited by theory, it is believed that agonists of the α7 nAChR (nicotinic acetylcholine receptor) subtype should be useful in the treatment or prophylaxis of psychotic disorders and intellectual impairment disorders, and have advantages over compounds which are or are also agonists of the α4 nAChR subtype. Therefore, compounds which are selective for the α7 nAChR subtype are preferred.

The pharmacological activity of the compounds of the invention may be measured in the tests set out below.

Test A
Assay for affinity at α7 nAChR subtype
$^{125}$I-α-Bungarotoxin (BTX) binding to rat hippocampal membranes Rat hippocampi were homogenized in 20 volumes of cold homogenization buffer (HB: concentrations of constituents (mM): tris(hydroxymethyl)aminomethane 50; $MgCl_2$ 1; NaCl 120; KCl 5: pH 7.4). The homogenate was centrifuged for 5 minutes at 1000 g, the supernatant was saved and the pellet re-extracted. The pooled supernatants were centrifuged for 20 minutes at 12000 g, washed, and resuspended in HB. Membranes (30–80 μg) were incubated with 5 nM [$^{125}$I]α-BTX, 1 mg/ml BSA (bovine serum albumin), test drug, and either 2 mM $CaCl_2$ or 0.5 mM EGTA [ethylene glycol-bis(β-aminoethylether] for 2 hours at 21° C., and then filtered and washed 4 times over Whatman glass fibre filters (thickness C) using a Brandel cell harvester. Pretreating the filters for 3 hours with 1% BSA/0.01% PEI (polyethyleneimine) in water was critical for low filter blanks (0.07 % of total counts per minute). Nonspecific binding was described by 100 μM (−)-nicotine, and specific binding was typically 75%.

Test B
Assay for affinity to the α4 nAChR subtype
[$^3$H]-(−)-nicotine binding

Using a procedure modified from Martino-Barrows and Kellar (Mol Pharm 31:169–174; 1987), rat brain (cortex and hippocampus) was homogenized as in the [$^{125}$I]α-BTX binding assay, centrifuged for 20 minutes at 12000 g, washed twice, and then resuspended in HB containing 100 μM diisopropyl fluorophosphate. After 20 minutes at 4° C., membranes (≈0.5 mg) were incubated with 3 nM [$^3$H]-(−)-nicotine, test drug, 1 μM atropine, and either 2 mM $CaCl_2$ or 0.5 mM EGTA for 1 hours at 4° C., and then filtered over Whatman glass fibre filters (thickness C) (pretreated for 1 hour with 0.5% PEI) using a Brandel cell harvester. Nonspecific binding was described by 100 μM carbachol, and specific binding was typically 84%.

Binding data analysis for Tests A and B $IC_{50}$ values and pseudo Hill coefficients ($n_H$) were calculated using the non-linear curve fitting program ALLFIT (DeLean A, Munson P J and Rodbard D (1977) Am. J. Physiol., 235:E97-E102). Saturation curves were fitted to a one site model, using the non-linear regression program ENZFITTER (Leatherbarrow, R. J. (1987)), yielding $K_D$ values of 1.67 and 1.70 nM for the $^{125}$I-α-BTX and [$^3$H]-(−)-nicotine ligands respectively. $K_i$ values were estimated using the general Cheng-Prusoff equation:

$$K_i = [IC_{50}]/((2+([ligand]/[K_D])^n)^{1/n} - 1)$$

where a value of n=1 was used whenever $n_H < 1.5$ and a value of n=2 was used when $n_H \geq 1.5$. Samples were assayed in triplicate and were typically ±5%. $K_i$ values were determined using 6 or more drug concentrations.

When compared with compounds of the prior art, the compounds of the invention have the advantage that they may be less toxic, be more efficacious, be longer acting, have a broader range of activity, be more potent, produce fewer side effects, are more easily absorbed or have other useful pharmacological properties.

The invention is illustrated by the following examples:

EXAMPLE 1

Spiro[1-azabicyclo[2.2.2]octane-3,5'-oxazolidine]-2'-one monohydrochloride (a) 2-(3-Hydroxy-1-azabicyclo[2.2.2]oct-3-yl)acetic acid $^t$butyl ester To a 0° C. solution of diisopropylamine (6.7 ml) in tetrahydrofuran (THF) (20 ml) was added 2.3M $^n$BuLi (20 ml). The reaction mixture was stirred for 40 minutes and then cooled to −78° C. To this mixture was added dropwise a solution of $^t$butylacetate (6.4 ml) in 10 ml of THF and stirring continued for an additional 15 minutes. Quinuclidin-3-one (free base) (5.0 g) in THF (15 ml) was added to the mixture dropwise and the mixture was allowed to warm to 0° C. over 1 hour. To this solution was added water (100 ml), the solution was extracted twice with chloroform and the combined extracts were washed once with brine. The resulting solution was dried over $MgSO_4$, filtered and dried in vacuo to give 9.53 g of the subtitle compound as an off-white solid.

(b) 2-(3-Hydroxy-1-azabicyclo[2.2.2]oct-3-yl)acetic acid hydrazide

To a solution of 3.5 g of the compound of step (a) in 15 ml of methylene chloride was added trifluoroacetic acid (39 ml) and the mixture was stirred at ambient temperature for three hours. The mixture was then concentrated in vacuo. The residue was dissolved in methanol (30 ml) and 18M $H_2SO_4$ (3 ml) was added and the mixture was stirred overnight. The mixture was then poured into a solution of sodium carbonate in water, extracted three times with chloroform, dried over $MgSO_4$, filtered and concentrated in vacuo to give a yellow solid. The solid was dissolved in methanol (10 ml) and hydrazine (2 ml) was added to this solution and the mixture was heated to reflux for one hour. The mixture was then concentrated in vacuo. The resulting solid was suspended in toluene (50 ml) and heated to reflux in an apparatus equipped with a Dean-Stark trap for two hours. The reaction mixture was then allowed to cool, and the product was filtered off to give 1.82 g of the subtitle compound as a tan solid.

(c) Spiro[1-azabicycyclo[2.2.2]octane-3,5'-oxazolidine]-2'-one monohydrochloride To a solution of 0.91 g of the compound of step (b) in water (7 ml) was added 12M HCl to give a solution with a pH of 1. The mixture was cooled to 0° C. and a 0° C. solution of sodium nitrite (0.33 g) in 5 ml of water was added. The solution was stirred at 0° C. for twenty minutes and then heated to 70° C. for an additional twenty minutes. The reaction mixture was cooled to ambient temperature and basified with 50% NaOH/$H_2O$. The solution was saturated with NaCl and extracted with chloroform 4×20 ml, dried over $MgSO_4$, filtered and concentrated in vacuo. The residue was dissolved in methanol and HCl gas was bubbled through the mixture until the pH was less than 2. Diethyl ether was added to the solution and the resulting white solid was filtered off to give 0.73 g of the title compound as an off-white solid, m.p. 289–291° C. $^1$H NMR (500 MHz, DMSO): 1.7–1.9 (m, 3H), 2.05 (m, 1H), 2.25 (bs, 1H), 3.15 (m, 3H), 3.2–3.35 (m, 1H), 3.4–3.6 (m, 3H), 3.6 (d, 1H), 7.75 (s, 1H), 10.95 (bs, 1H).

EXAMPLE 2

(+)- and (−)-Spiro[1-azabicyclo[2.2.2]octane-3,5'-oxazolidine]-2'-one monohydrochloride To a solution of the compound of Example 1 (3.8 g) in absolute ethanol was added a solution of dibenzoyl-L-tartaric acid (7.474 g) in absolute ethanol and to this mixture was added a small portion of ethyl acetate. A solid formed upon standing within an hour which was filtered off and the filtrate retained. The solid was dissolved in aqueous sodium hydroxide, extracted with chloroform 3×50 ml, dried over $MgSO_4$, filtered and concentrated in vacuo. The residue was dissolved in methanol and HCl gas was bubbled through the mixture until the pH was less than 2. Diethyl ether was added to the solution and the resulting white solid was filtered off to give 0.63 g of the (+)-enantiomer, m.p. >250° C. $[\alpha]_D$=+57.978 (c=0.6570, $CH_3OH$).

The filtrate retained above was converted to the free base by concentrating the solution and then dissolving the residue in 20% NaOH/$H_2O$, which was extracted with chloroform, dried over $MgSO_4$, filtered and concentrated in vacuo to give 1.21 g of residue. The residue was dissolved in absolute ethanol and combined with a solution of 2.38 g of dibenzoyl-D-tartaric acid in absolute ethanol. The mixture was stirred and a small portion of ethyl acetate added resulting in the formation of a white solid after stirring for an hour. The precipitate was filtered and dissolved in 20% NaOH/$H_2O$, extracted with chloroform, dried over $MgSO_4$, filtered and concentrated in vacuo. The residue was dissolved in methanol and HCl gas was bubbled through the mixture until the pH was less than 2. Diethyl ether was added to the solution and the resulting white solid was filtered off to give 0.21 g of the (−)-enantiomer, m.p. >250° C. $[\alpha]_D$=−61.473 (c=0.7727, $CH_3OH$).

EXAMPLE 3

Spiro[1-azabicyclo[2.2.]heptan-3,5'-oxazolidin-2'-one] monohydrochloride (a) 3-Hydroxy-1-azabicyclo[2.2.1]hept-3-yl acetic acid ethyl ester To a cooled (−78° C.) solution of diisopropylamine (2.65 ml, 0.0203 moles) in tetrahydrofuran (150 ml) was added 2.5M n-BuLi in hexanes (8.1 ml, 0.0203 moles) dropwise over one minute. After ten minutes, ethyl acetate (1.97 ml, 0.0203 moles) was added dropwise over one minute. After a further ten minutes, 1-azabicyclo[2.2.1]heptan-3-one (1.5 g, 0.0135 moles, prepared by the method of J Chem Soc, Chem Commun, 1618, 1988) in tetrahydrofuran (25 ml) was added dropwise over five minutes. After twenty five minutes, the cold bath was removed and the mixture was allowed to warm to ambient temperature. To this mixture was added water (100 ml) followed by chloroform (250 ml). The organic layer was separated and the aqueous layer was extracted with chloroform (100 ml). The combined organic extracts were dried over $MgSO_4$, filtered and concentrated in vacuo to give the subtitle compound (1.12 g).

(b) 3-Hydroxy-1-azabicyclo[2.2.1]hept-3-yl acetic acid hydrazide

To a solution of the product of step (a) (1.12 g, 0.0056 moles) in methanol (20 ml) at room temperature was added anhydrous hydrazine (1.76 ml, 0.056 moles) and the mixture was stirred overnight. The mixture was concentrated in vacuo and azeotroped twice with toluene (100 ml) by heating to reflux in an apparatus fitted with a Dean-Stark trap to give the subtitle compound (1.11 g).

(c) Spiro[1-azabicyclo[2.2.1]heptan-3.5'-oxazolidin-2'-one] monohydrochloride

To a cooled (0° C.) solution of the product of step (b) (1.11 g, 0.006 moles) in water (50 ml) adjusted to pH 1 with concentrated HCl was added dropwise over two minutes an aqueous solution of $NaNO_2$ (0.455 g, 0.0066 moles). After the addition was complete the cold bath was removed and the mixture was heated to 85° C. for one hour. The mixture was allowed to cool to ambient temperature and basified to pH 10 with 50% NaOH/$H_2O$. This mixture was extracted three times with chloroform (150 ml), dried over $MgSO_4$, filtered and concentrated in vacuo. The residue was flash chromatographed on silica gel with methanol/ethyl acetate [1:1]. The appropriate fractions were collected and concentrated. The residue was then dissolved in chloroform, filtered and concentrated in vacuo. The residue was dissolved in ethyl acetate/methanol and treated with a saturated solution of HCl/ethyl acetate until the solution had a pH<6. The solution was concentrated to give 120 mg of residue. This residue was dissolved in hot methanol and precipitated with ether to give the title compound (28 mg), m.p. >250° C. $^1$H NMR (500 MHz, DMSO): 1.95 (m, 1H), 2.1 (m, 1H), 3.0 (s, 1H), 3.2–3.4 (m, 5H), 3.5–3.6 (m, 3H), 7.8 (s, 1H), 10.6 (bs, 1H).

EXAMPLE 4

3'-Methyl spiro-[1-azabicyclo[2.2.2]octan-3,5'-oxazolidin-2'-one] monohydrochloride (a) Spiro-1-azabicyclo[2.2.2]octan-3-oxirane To a suspension of sodium hydride (11.6 g of 60% oil dispersion washed 3× with hexane; 0.35 mol) in 600 mL of DMSO was added 101.4 g (0.35 mol) of trimethylsulfoxonium iodide in portions. After gas evolution had subsided, the mixture was stirred at room temperature for 30 min. A solution of quinuclidin-3-one (44 g, 0.35 mol) in 200 mL of THF was added dropwise over a period of 30 min and the mixture was warmed to 70–80° C. for 1 h. The reaction mixture was cooled to RT, poured onto 1 L of ice water and the aqueous solution extracted with $CHCl_3$ (4×300 mL). The organic extracts were washed with $H_2O$ (3×500 mL), saturated brine (1×300 mL), dried over $MgSO_4$ and the solution evaporated to afford the subtitle compound as a yellow oil (37.6 g, 77%).

(b) 3-Hydroxy-1-azabicyclo[2.2.2]oct-3-yl methylaminomethane

To a solution of 25 mL (0.72 mol) of condensed methylamine in 75 mL of methanol was added 10.2 g (0.073 mol) of the product of step (a) and the solution stirred at room temperature for 16 h. The reaction mixture was concentrated under reduced pressure and the resulting oil was dissolved in 75 mL of CHCl₃ and concentrated to afford 12.4 g (100%) of the subtitle compound as an oil.

(c) 3'-Methyl spiro-[1-azabicyclo[2.2.2]octan-3,5'-oxazolidin-2'-one] monohydrochloride To a solution of the product of step (b) (8.0 g, 0.047 mol) in 100 mL of dry THF was added 9.15 g (0.056 mol) of carbonyldiimidazole and the mixture was heated at reflux for 3 h. The reaction mixture was then cooled to room temperature and concentrated under vacuum. The residual oil was dissolved in 200 mL of CH₂C₂, the solution washed with H₂O (1×100 mL), brine (1×50 mL), dried over MgSO₄ and evaporated to afford a yellow solid. The solid was dissolved in 50 mL of 1:1 methanol/isopropanol mixture, acidified with HCl in methanol, and the precipitate collected, washed with cold methanol and dried to afford 5.6 g (51%) of the title compound as a colorless solid, m.p. 305–307° C. ¹H NMR (500 MHz, DMSO): 1.8 (m, 3H), 2.05 (m, 1H), 2.25 (bs, 1H), 2.75 (s, 3H), 3.1–3.2 (m, 3H), 3.25–3.35 (m, 1H), 3.4–3.5 (m, 1H), 3.5–3.6 (m, 2H), 3.7 (d, 1H), 10.9 (bs, 1H).

EXAMPLE 5

The compounds spiro[1-azabicyclo[2.2.2]octane-3,5'-oxazolidine]-2'-one monohydrochoride, (+)-spiro[1-azabicyclo[2.2.2]octane-3,5'-oxazolidine]-2'-one monohydrochloride, (−)-spiro[1-azabicyclo-[2.2.2]octane-3,5'-oxazolidine-2'-one monohydrochloride,spiro[1-azabicyclo[2.2.1]heptan-3,5'-oxazolidin-2'-one] monohydrochloride and 3'-methyl spiro-1-azabicyclo[2.2.2]octan-3,5'-oxazolidin-2'-one monohydrochloride were tested in Test A above and gave binding affinities (K$_i$) of less than 10 μM indicating that they are expected to have useful therapeutic activity.

The compounds spiro[1-azabicyclo[2.2.2]octane-3,5'-oxazolidine]-2'-one monohydrochoride, (+)-spiro[1-azabicyclo[2.2.2]octane-3,5'-oxazolidine]-2'-one monohydrochloride, (−)-spiro[1-azabicyclo-[2.2.2]octane-3,5'-oxazolidine]-2'-one monohydrochloride, spiro-1-azabicyclo[2.2.1]heptan-3,5'-oxazolidin-2'-one] monohydrochloride and 3'-methyl spiro-1-azabicyclo[2.2.2]octan-3,5'-oxazolidin-2'-one monohydrochloride were tested in Test B above and gave K$_i$ values at least 1.6 times greater than those given in Test A indicating that they possess desirable selectivity.

We claim:

1. A compound of formula I:

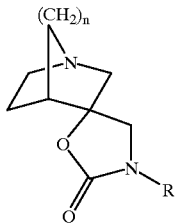

wherein
R represents hydrogen or methyl; and
n represents 1 or 2;
or a pharmaceutically acceptable acid addition salt or enantiomer thereof.

2. A compound according to claim 1 wherein R represents hydrogen, or a pharmaceutically acceptable acid addition salt or enantiomer thereof.

3. Spiro[1-azabicyclo[2.2.2]octane-3,5'-oxazolidine]-2'-one, or a pharmaceutically acceptable acid addition salt or enantiomer thereof.

4. (+)-Spiro[1-azabicyclo[2.2.2]octane-3,5'-oxazolidine]-2'-one, or a pharmaceutically acceptable acid addition salt thereof.

5. (−)-Spiro[1-azabicyclo[2.2.2]octane-3,5'-oxazolidine]-2'-one, or a pharmaceutically acceptable acid addition salt thereof.

6. Spiro[1-azabicyclo[2.2.1]heptan-3,5'-oxazolidin-2'-one, or a pharmaceutically acceptable acid addition salt or enantiomer thereof.

7. 3'-Methyl spiro-[1-azabicyclo[2.2.2]octan-3,5'-oxazolidin-2'-one], or a pharmaceutically acceptable acid addition salt or enantiomer thereof.

8. A pharmaceutical formulation including a compound as defined in any one of claims 1 to 7, or a pharmaceutically acceptable acid addition salt or enantiomer thereof, in admixture with a pharmaceutically acceptable diluent or carrier.

9. A method of treatment or prophylaxis of attention deficit hyperactivity disorder, which comprises administering a therapeutically effective amount of a compound as defined in any one of claims 1 to 7, or a pharmaceutically acceptable acid addition salt or enantiomer thereof, to a patient.

10. A method of treatment or prophylaxis of anxiety, which comprises administering is a therapeutically effective amount of a compound as defined in any one of claims 1 to 7, or a pharmaceutically acceptable acid addition salt or enantiomer thereof, to a patient.

11. A process for preparation of a compound of formula I, as defined in claim 1, or a pharmaceutically acceptable acid addition salt or enantiomer thereof, which comprises:

(a) preparing a compound of formula I in which R represents hydrogen by cyclising a corresponding compound of formula II

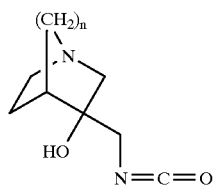

wherein n is as defined in claim 1;

(b) preparing a compound of formula I by reacting a corresponding compound of formula III

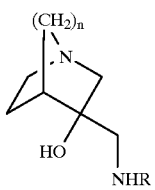

wherein n and R are as defined in claim 1, with a carbonylating agents;

(c) preparing a compound of formula I in which R represents methyl by alkylating a corresponding compound of formula I in which R represents hydrogen; or (d) preparing one enantiomer of a compound of formula I by resolving the one enantiomer from a mixture of enantiomers;

and where desired or necessary converting the resultant compound of formula I, or an acid addition salt or enantiomer thereof, to a pharmaceutically acceptable acid addition salt or enantiomer thereof, or vice versa.

12. A compound of formula IV

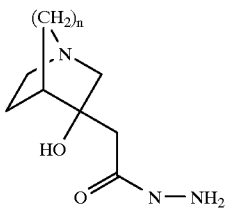

IV wherein n is 1 or 2, or a salt or enantiomer thereof.

13. A method of treatment or prophylaxis of schizophrenia, which comprises administering a therapeutically effective amount of a compound as defined in any one of claims 1 to 7, or a pharmaceutically acceptable acid addition salt or enantiomer thereof, to a patient.

14. A compound of formula III

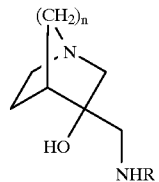

III wherein n is 1 or 2 and R represents methyl, or a salt or enantiomer thereof.

* * * * *